US007651485B2

(12) United States Patent
Fattman

(10) Patent No.: US 7,651,485 B2
(45) Date of Patent: Jan. 26, 2010

(54) OSTOMY POUCH ADHESIVES SUCH AS POLYSILOXANES THAT ARE RESISTANT TO STOMAL EFFLUENT

(75) Inventor: George F. Fattman, Mt. Laurel, NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 10/715,730

(22) Filed: Nov. 18, 2003

(65) Prior Publication Data

US 2004/0102744 A1 May 27, 2004

Related U.S. Application Data

(60) Provisional application No. 60/429,505, filed on Nov. 27, 2002.

(51) Int. Cl.
*A61F 5/44* (2006.01)

(52) U.S. Cl. ....................... 604/344; 604/304; 604/332; 604/339; 604/391; 604/336; 604/342; 428/391

(58) Field of Classification Search ................. 428/391; 604/307, 332, 339, 344, 391
See application file for complete search history.

(56) References Cited

U.S. PATENT DOCUMENTS 1,274,382 A 8/1918 Burgoyne
2,341,984 A * 2/1944 Graves ....................... 604/332
2,662,525 A * 12/1953 Priebe ....................... 604/332
2,676,182 A * 4/1954 Daudt et al. ................ 556/453
3,385,298 A * 5/1968 Fenton ....................... 604/332
3,983,298 A * 9/1976 Hahn et al. ........... 428/355 RA
4,039,707 A * 8/1977 O'Malley ................. 428/41.8
4,411,659 A * 10/1983 Jensen et al. ................ 604/332
4,445,898 A * 5/1984 Jensen ........................ 604/337
4,475,908 A * 10/1984 Lloyd ......................... 604/339
4,551,490 A * 11/1985 Doyle et al. .................. 524/22
4,650,817 A 3/1987 Allen et al.
4,701,169 A 10/1987 Steer
4,775,374 A * 10/1988 Cilento et al. ............... 604/344
4,808,173 A 2/1989 Kay
4,826,495 A 5/1989 Petersen
4,831,070 A * 5/1989 McInally et al. ............ 524/267
4,890,608 A * 1/1990 Steer ........................... 602/57
5,125,917 A * 6/1992 Whealin ..................... 604/340
5,160,330 A 11/1992 Cross
5,346,482 A 9/1994 Metz et al.
5,429,626 A 7/1995 Fenton
5,496,296 A 3/1996 Holmberg
5,556,636 A 9/1996 Yano et al.
5,580,915 A * 12/1996 Lin ............................ 524/267
5,709,673 A * 1/1998 Keyes ........................ 604/332
5,722,965 A 3/1998 Kuczynski
5,800,415 A 9/1998 Olsen
6,520,943 B1 * 2/2003 Wagner ...................... 604/338

FOREIGN PATENT DOCUMENTS

| | | | | |
|---|---|---|---|---|
| EP | 0315333 | A | | 5/1989 |
| GB | 1571657 | | * | 7/1980 |
| WO | WO 8600532 | A1 | * | 1/1986 |
| WO | WO 97/35534 | | | 10/1997 |
| WO | WO 98 55157 | A | | 12/1998 |
| WO | WO 9855157 | A2 | * | 12/1998 |
| WO | WO 00/26565 | | | 5/2000 |
| WO | WO 00/30576 | | | 6/2000 |
| WO | WO 00/67683 | | | 11/2000 |
| WO | WO 01/85074 | | | 11/2001 |

OTHER PUBLICATIONS

Handbook of Pressure Sensitive Adhesive Technology, pp. 38-39, 61, 66-67.
Abdominal Stomas and their Skin Disorders, p. 50.

* cited by examiner

*Primary Examiner*—Tatyana Zalukaeva
*Assistant Examiner*—Ginger T Chapman
(74) *Attorney, Agent, or Firm*—Stuart E. Krieger

(57) ABSTRACT

An ostomy device having a pressure sensitive adhesive comprising a polysiloxane, or a polysiloxane and a silicate resin including their blends and reaction products.

17 Claims, No Drawings

OSTOMY POUCH ADHESIVES SUCH AS POLYSILOXANES THAT ARE RESISTANT TO STOMAL EFFLUENT

This application claims the benefit of U.S. Provisional Application No. 60/429,505 filed Nov. 27, 2002 and is hereby incorporated by reference in its entirety.

BACKGROUND

The objects of the invention are pressure sensitive adhesive compositions that have improved resistance to intestinal fluid and ostomy devices utilizing these adhesives for attachment to the body, collection of intestinal fluid or collection of effluent from a stoma.

The most common commercial ostomy devices have two basic requirements for acceptable performance, attachment of the device to the peristomal area and containment of effluent from the stoma. These requirements are met by two discreet components of the device, referred to as the base plate, body wafer or wafer (for attachment) and the pouch or bag (for collection). The wafer and pouch work together to protect the peristomal skin and provide a secure means for discrete collection and disposal of effluent.

The wafer and pouch components may be coupled together by a variety of means including thermal, ultrasonic, radio frequency, or other kinds of plastic welds, hot melt or reactive or curable glues, pressure sensitive adhesives, and various mechanical means. When these components are permanently joined together, for example when the coupling mechanism is a plastic weld or glue joint, then the product is considered a one piece appliance. Two piece appliances are devices in which the pouch and wafer components can be separated while preserving the usefulness of one or both components. Two piece devices can be made using coupling mechanisms based on pressure sensitive adhesives or from mechanical couplings of various designs. An example of a mechanical coupling is described by British Patent specification GB 1 571 657.

Both one piece and two piece ostomy devices have advantages and disadvantages. The one piece design is typically very flexible, conforms well to the body, and is less noticeable under clothing compared with two piece products which tend to be more rigid and higher profile. In a two piece design, the wafer can be separated, from a pouch and reconnected with the same or different pouch. The two piece design offers several advantages, the primary one being that the pouch can be removed and changed without having to change the wafer, which requires additional work and stresses the skin. Other advantages of the two piece design are that the stoma and peristomal area can be observed and, if needed, treated without removing the wafer or destroying the pouch. One piece products generally do not provide these advantages.

The coupling mechanism is of significant importance in determining the usefulness of an ostomy device since it strongly influences the flexibility, convenience, and versatility of the device. It also impacts the most important need for the wearer, containment of effluent. Like the other components of the device, the coupling must contain all effluent from the stoma, which may be emitted in solid, liquid or gaseous forms. Permanent couplings like thermal welds between the wafer and pouch are simple and effective mechanisms for reliable containment of stoma output but suffer the drawbacks of the one piece design. For this reason ostomy devices having two piece mechanical couplings are sometimes preferred. However, mechanical couplings are typically more rigid and have a higher profile than the couplings of one piece designs, and can be uncomfortable and less discrete for the wearer. They also require sufficient manual dexterity and visual acuity to properly assemble or disassemble. However, a properly designed mechanical coupling like the one described in GB 1 571 657 yields a pouch to wafer connection that provides excellent security and containment characteristics.

Coupling mechanisms based on bonding together an ostomy pouch and wafer using pressure sensitive adhesives can combine the advantages of both one piece and two piece designs if they enable repeatable and secure attachment of the pouch and wafer, yield a low profile device, and provide reliable containment of effluent. A pressure sensitive adhesive based ostomy device coupling is defined herein as comprising a pressure sensitive adhesive, in adhesive contact with the surface of at least one other ostomy device component.

There are numerous prior art disclosures that describe the use of adhesives in ostomy device couplings. UK Patent 1,274,382 discloses a post surgical drainage device for receiving discharge from a surgical wound or stoma, and an attachment means for securing that device to the patient's body. The attachment means is comprised of two laminar parts assembled in face to face relationship. The first part of the attachment means comprises an adhesive for securing the attachment means to the body. The second part of the attachment means is a flexible plastic sheet that secures to the pouch by means of an adhesive.

U.S. Pat. No. 4,701,169 discloses an ostomy appliance comprising a body-attachable pad and a means whereby a plurality of ostomy bags can be adhesively attached to the pad in sequence by exposing a fresh layer of adhesive each time it is desired to attach a clean bag.

U.S. Pat. No. 5,160,330 discloses a water closet disposable pouch having an adhesive disc secured to an inside wall of the bag for use in connecting the bag to a flange worn on the body.

U.S. Pat. No. 5,496,296 discloses an adhesively coupled ostomy pouch and faceplate device wherein the faceplate contains an adhesive that may be squeezed out from a compartment in the faceplate to form a peristomal gasket.

U.S. Pat. No. 5,709,673 discloses a flushable ostomy pouch of either a one piece or two piece design wherein the two piece design includes an adhesive coupling to join together the wafer and pouch.

U.S. Pat. No. 5,722,965 discloses an adhesively coupled ostomy device comprising a repositionable foam tape that inhibits the formation of wrinkles in the coupling mechanism.

Patent Application WO99/26565 discloses an ostomy system comprising a pouch that is adhesively coupled to a mounting wafer. The mounting wafer has a landing zone film of releaseable plastic. The landing zone has one portion that is immovable with respect to the body surface and another part that is deflectable away from the body surface to which it is attached.

Patent application WO00/30576 discloses an ostomy appliance comprising a body side member and a receiving bag each including a flange said to be designed for removable adhesive connection of the appliance components wherein the collecting bag flange incorporates perforations to reduce the risk of leakage.

Patent application WO01/85074 discloses a carrier device comprising a base plate with flange for adhesive connection with an ostomy collecting bag wherein the outer portion of the flange is free to move relative to the base plate.

The preceding patents and patent applications all disclose ostomy device couplings in which both the body attaching and effluent collecting components have essentially only planar regions whereby they are attached together using an adhesive. There are additional prior art disclosures that describe ostomy device couplings made from flexible components that are substantially non-planar and which function by being assembled in more than two dimensions. U.S. Pat. No. 4,808,173 discloses a coupling ring assembly for an ostomy device in which one of the rings has a radially-facing annular channel for receiving a latching flange of another ring. A deformable, viscoelastic polymeric material lines the channel where the two coupling rings are attached. It is stated that additional security may be obtained if the liner also has adhesive properties.

U.S. Pat. No. 4,826,495 discloses a water closet flushable ostomy bag and a retainer plate to which it may be coupled by means of a pressure sensitive adhesive. The retainer plate includes a hollow bead projecting into the pouch which is said to provide a passage way for flatus to pass out of the pouch.

U.S. Pat. No. 5,429,626 discloses an ostomy appliance having a mounting member for attachment to the skin, the mounting member comprising a rigid mounting plate on its distal side and an axially extending curb for alignment of the pouch. The pouch is provided with an annular band of adhesive to removably adhere it to the mounting plate.

U.S. Pat. No. 5,346,482 discloses a two piece ostomy appliance comprising a flushable pouch that may be attached to an ostomy faceplate with an adhesive. The faceplate component has an axially extending protective collar that inserts into the pouch to shield water-soluble layers of the pouch from the fluids that enter it.

Patent Application WO97/35534 discloses a coupling device for mounting an ostomy bag to the body comprising annular sealing elements and annular bonding regions on both the pouch and wafer. At least one of the bonding regions is provided with a layer of repositionable adhesive. The sealing elements are said to cooperate to form a water tight seal while the bonding regions form a releaseable bond.

U.S. Pat. No. 5,800,415 discloses an ostomy collecting system comprised of a collecting bag and a base plate, each of which has an annular flange for adhesive coupling. Also disclosed is an axially extending collar that acts as a guide surface to prevent improper mounting of the bag and which forms a passage for the stoma, providing protection of the coupling adhesive from stomal effluent.

DESCRIPTION OF THE INVENTION

The object of the invention includes an ostomy device with pressure sensitive adhesive compositions having improved resistance to intestinal fluid or effluent from a stoma. These adhesive compositions may be used to couple a fluid or effluent collecting device component to a body attaching device component. They may also be used to attach any components of the device that may be exposed to stomal effluent. Finally, they may be used to attach an ostomy device directly to the skin, either as a one piece or a two piece device. In this case the adhesive function as the skin attaching component, i.e. the skin barrier or wafer.

It is generally known that intestinal fluids can vary greatly in their ability to attack the component materials of ostomy devices. It is believed that the variation in potency of intestinal fluids derives from many factors that influence the strength of their surface and enzymatic activities. These factors vary from individual to individual according to physiological factors and diet, among other causes. Another factor affecting the performance of ostomy devices is the wearing time during which the device is in contact with effluent. As a result, the same component designs and materials may be satisfactory for some individuals and unacceptable for others. Accordingly, the ability of a coupling device to provide sufficient containment of stoma effluent also varies according to its design and composition.

When a containment failure occurs in an ostomy device coupled by either plastic welds or by a mechanical means it is usually an unforeseen catastrophic failure that happens without warning. In contrast it has been found that ostomy devices coupled by pressure sensitive adhesives tend to lose containment over a longer period of time. Leaking may not occur all at once but can happen gradually by a migration of the intestinal fluid across the adhesively bonded interface. Those skilled in the art recognize that the strength of an adhesive bond is usually measured by peeling it from its adherend. Bond strength is a strong function of the application pressure used to create the bond and the amount of time that pressure is maintained. For pressure sensitive adhesive couplings used to connect an ostomy device component, it would be expected that the adhesives with higher bond strength would better contain the contents of an ostomy device. However, it has surprisingly been found that the chemical composition of the adhesive is a more significant factor.

The present invention includes the composition of a resealable adhesive coupling that is very resistant to intestinal fluids and very effective in ostomy devices. Of the 15 adhesive coupling patents or applications reviewed above, five are silent as to the composition of the adhesive. Eight suggest the general suitability of acrylic adhesives for ostomy couplings, particularly the grades of these adhesives indicated for contact with the skin. The remaining two suggest the use of hot melt adhesives, although the design of the couplings in these patents includes axially extended components of the coupling, which alleviates stress on the adhesive. The prior art does not disclose the present adhesives that are suitable for ostomy device couplings and are very resistant to intestinal fluid. It appears that some of the earlier couplings are designed in a manner to compensate for the adhesive's inability to resist intestinal fluid. These axially extended designs also have a higher profile for the wearer and suffer the disadvantages of being difficult to assemble for the visually or dexterously impaired, more noticeable to others, less flexible to the wearer, or all of the above.

Examples of the prior art include U.S. Pat. No. 5,496,296, which suggests the use of a conventional medical grade acrylic adhesive. Another example of an adhesive coupling based on acrylic polymers is disclosed in U.S. Pat. No. 5,722,965 which describes a resealable foam tape with a hypoallergenic acrylic adhesive. Some acrylic adhesives have been found to yield an ostomy device that successfully contains stomal effluent for a few days. However, during that time effluent can be observed to migrate slowly across the adhesively coupled interface, again depending on physiological factors, often beginning on the first day. As the migrating front approaches the radial edge of the coupling there is less and less adhesive in contact with the mating surfaces of the coupling, the coupling is less and less secure, and a leak is more and more imminent. An actual leak or the threat of an impending leak is incompatible with the satisfactory performance of the product. For longer wearing times or for individuals with more aggressive effluent an improvement would be obtained if the coupling retarded or eliminated stool migration and/or the leakage of effluent within the coupling interface.

In order to evaluate the performance of various adhesives for their ability to resist intestinal fluids, a laboratory test was developed using Simulated Ileo Fluid (SIF), a variation of the intestinal fluid test solution found in the United States Pharmacopeia. A testing jig was made from a PET sheet to which was attached an ostomy wafer of the design disclosed in Patent Application WO99/26565. Ostomy pouches of the design disclosed in Patent Application WO99/26565 were attached by an adhesive coupling onto the wafer landing zone comprised of poly (ethylene-co-vinyl acetate) film. This EVA film contains 9% vinyl acetate comonomer.

For each test, up to 10 pouches were then filled with 200 grams of SIF at various concentrations, sealed and inverted so that contact between their contents and the coupling interface would be continuous and intimate. Pouches were either suspended on a moving wall or laid flat. Environmental conditions were maintained at a temperature of 40 C and not less than 75% relative humidity to simulate conditions of use.

After approximately 12-24 hours the pouches were removed from their environmental chamber and returned to the laboratory for evaluation of the resistance of the coupling to the simulated ileo fluid. Testing was conducted at various concentrations of SIF to account for individual variations in stomal output. Ratings of migration were made according to the radial distance traveled by the SIF through the coupling system. The radial distance from inner diameter to outer diameter of the coupling is approximately one inch. The following results were obtained.

TABLE 1

Migration Results

| SIF Concentration | Low | Medium | High |
|---|---|---|---|
| Typical Migration Ratings for ostomy device disclosed in WO99/26565 | 0-1 | 1-3 | 3-5 |

TABLE 2

Migration Test Rating Scale

| Rating Scale | 0 | 1 | 2 | 3 | 4 | 5 |
|---|---|---|---|---|---|---|
| Migration Distance | None | Up to 0.125 inches from coupling ID | Up to 0.25 inches from coupling ID | Up to 0.5 inches from coupling ID | Migrated to outer edge of coupling | Leaked through coupling entirely |

Additional pouches were produced according to the design disclosed in WO99/26565 with the exception that the adhesive component of the pressure sensitive adhesive coupling was replaced with various other adhesives according to the following tables. These pouches were tested according to the method described above. In some cases the adhesive coupling was adhered directly to an EVA sheet without an ostomy wafer being used, the sheet having composition and dimensions equivalent to those of the wafer attachment component. In that case the EVA sheet to which the pouch was attached was then further adhered to the test jig on its side opposite from the pouch. The EVA sheet was approximately 0.010 inches thick, comprised of polyethylene with 9% vinyl acetate comonomer (polyethylene vinyl acetate), and was the primary attachment point on the body wafer, sometimes referred to as a landing zone. The results are listed in Table 1. A migration result is shown for each individual pouch tested at the condition indicated.

TABLE 3

Migration Ratings for Various Adhesives Evaluated for Ostomy Couplings

| Adhesive ID | Adhesive Component | CSIF Concentration Low | Medium | High |
|---|---|---|---|---|
| [1]Duro-Tak ® 87-4098 | Polyacrylate | 0, 0, 0 | 3, 2, 1 | 4, 4, 4 |
| [1]Duro-Tak ® 87-9085 | Polyisobutylene | 1, 1, 1 | 2, 3, 2 | 3, 4, 3 |
| [1]Duro-Tak ® 87-9301 | Polyacrylate | 2, 2, 2 | 3, 3, 3 | 3, 4, 4 |
| [1]Duro-Tak ® 87-9088 | Polyacrylate | 1, 1, 1 | 3, 2, 2 | 5, 5, 5 |
| [2]GMS 2999 | Polyacrylate | 2, 1, 2 | 2, 2, 2 | 3, 3, 3 |
| [2]GMS 1753 | Polyacrylate | 1, 1, 0 | 4, 3, 3 | 3, 5, 5 |
| [2]GMS 2495 | Polyacrylate | 0, 1, 2 | 3, 3, 3 | 5, 5, 5 |
| [2]GME 2484 | Polyacrylate | 4, 5, 5 | 5, 5, 5 | 5, 5, 5 |
| [2]GME 3060 | Polyacrylate | 5, 5, 5 | 5, 5, 5 | 5, 5, 5 |
| [3]HL 2816 | Styrenic Block Copolymer | NA | NA | 5, 5, 5 |
| [3]HL-2110 | Styrenic Block Copolymer | 5 | NA | 5 |
| [3]HL-2198 | Styrenic Block Copolymer | 5 | NA | 5 |
| Proprietary Formula | Hydrogel | 5, 5, 5 | 5, 5, 5 | 5, 5, 5 |
| Proprietary Formula | Polyisobutylene | 5 | 5 | 5 |

[1]Duro-Takθ is a trademark of the National Starch and Chemical Company (Division of ICI).
[2]GMS and GME stand for Gelvaθ Multipolymer Solution and Gelvaθ Multipolymer Emulsion, trademarks of Solutia, Inc.
[3]H. B. Fuller Company
[4]Proprietary formulation of a conductive hydrogel polymer.
[5]Proprietary formulation of polyisobutylene adhesive The results in Table 3 show that all of the adhesives exhibited significant migration of SIF through the adhesive coupling at the interface between the adhesive and the EVA sheet. Migration was found to depend on the chemical composition of the adhesive itself and appeared to be independent of the level of adhesion between the coupling components.

Additional testing was conducted in order to discover adhesives that would prevent migration through the coupling. The best performing adhesive was comprised of a silicone polymer. Pouches were produced according to the design disclosed in WO 99/26565 with the exception that the adhesive component of the pouch coupling was replaced with a medical grade silicone adhesive. These pouches were tested according to the method described above.

TABLE 4

Migration Ratings for Coupling Adhesives that Resist Intestinal Fluid

| Adhesive ID | Adhesive Component | CSIF Concentration Low | Medium | High |
|---|---|---|---|---|
| Adhesive with Bio-PSA ® 7-4601 | Polysiloxane | 0, 0, 0 | 0, 0, 0 | 0, 0, 0 |

Table 5 shows the results of additional testing according to the method above but using higher concentrations of CSIF.

TABLE 5

Migration Testing with 8 Times Original High Concentration

| CSIF Concentration | 8 × High* |
|---|---|
| Migration Rating for ostomy device disclosed in WO 99/26565 | All Leaked |
| Migration Rating for ostomy device design per WO 99/26565 with silicone pressure sensitive adhesive | All 0 |

*High concentration refers to the same high concentration as used in Tables 1, 3 and 4 above.

The results in Tables 4 and 5 demonstrate the surprising result that the silicone based adhesive significantly outperformed the acrylic adhesive disclosed in WO 99/26565, as well as all 14 of the other adhesive formulations evaluated in Table 3 above. The pouches with silicone adhesive coupling continued to resist the CSIF even when pouches were allowed to remain in their environmental chamber and exposed to the CSIF for as long as one week.

Based on the results above it has been discovered that ostomy coupling devices comprised of silicone adhesives are a dramatic improvement over the prior art. It is also believed that silicone adhesives are effective ostomy skin barriers on their own, in part due to its resistance to intestinal fluid. For ostomy devices of the one piece design the silicone adhesive attaches the pouch directly to the skin. For ostomy devices of the two piece design the silicone adhesive forms a skin barrier wafer that may be coupled to a collection device. In each case the silicone adhesive protects peristomal skin and may be used to secure a collection device around the stoma.

Satisfactory resistance to intestinal fluid is of paramount importance for the performance of an ostomy skin barrier adhesive since in that case any migration of intestinal fluid will occur at the interface between the skin barrier and the skin of the device wearer. It is well known that intestinal fluid has a disastrous effect on the health of peristomal skin. Because of the presence of proteolytic enzymes, stomal effluent causes irritation, maceration, excoriation and possibly digestion of skin. While these problems typically are more severe for ileostomates they occur for urostomates and colostomates as well. Damaged skin can be more difficult for the adhesive to bond with, leading to a vicious cycle of more and more skin exposure and worsening skin damage. Because of their resistance to intestinal fluids silicone adhesives are a significant improvement over prior art ostomy devices.

Silicone adhesives are typically comprised of two major components, a siloxane polymer and a silicate resin. Siloxane polymers have alternating silicone and oxygen atoms along their main chain. They cover a wide range of molecular weight, from as low as the dimer, hexamethylene disiloxane, to as much as one million. As their molecular weight increases the viscosity of the polymer becomes very high, exceeding 10,000,000 centistokes. Examples of polymers used in silicone adhesives include polydimethylsiloxane, polymethylphenylsiloxane, polydimethyldiphenylsiloxane, and other silicone polymers including alkylsiloxanes and organosiloxanes that are described generally as polysiloxanes. Hydrophillicity of polysiloxanes can be adjusted and controlled by modifying or copolymerizing them with an alkylene oxide. Another option would be to blend the silicone adhesives with hydrocolloids so that the adhesive include from about 5% to about 65% hydrocolloids.

An example of a silicate resin is tetrakis (trimethylsiloxy) silicate. Either the polysiloxane or the resin or both may have silanol functionality. For the silicate resin tetrakis (trimethylsiloxy), silanol functionality results in the replacement of one or more of the trimethylsiloxy groups with hydroxyl groups. During manufacture of the polysiloxane adhesive, processing conditions are controlled so that a chemical reaction, for example a condensation reaction or an addition reaction, occurs to yield a network of polysiloxane chains cross linked with the resin. Cross linking results in the rheological properties necessary to achieve satisfactory tack, peel and cohesive properties. A catalyst, for example benzoyl peroxide may be added to enhance the crosslinking reaction.

Silicone adhesives of the kind described above may be obtained commercially in several forms. Those available include one part adhesives manufactured as cross linked polymers in hydrocarbon solvent, or two part adhesive systems that are solvent free. In that case the polymer, resin and catalyst are thoroughly mixed and cured just prior to use. The one part and two part adhesives described are typically coated onto the adhesive substrate and heated to obtain the desired adhesive properties. Alternatively, silicone adhesives may be extrusion processed as for a pressure sensitive hot melt. Key parameters that control the adhesive properties include molecular weight of the polymer, ratio of polymer to resin, and degree of crosslinking, the later of which can be controlled by the degree of silanol (hydroxyl) functionality available in either the resin, the polysiloxane, or both. A wider range of formulations than those available commercially can be obtained by blending the commercial adhesive grades with additional polysiloxanes including polydimethylsiloxane silicone oils and other silicone fluids, silicate resins, and catalysts, for example organic peroxides or benzoyl peroxide. Properties of the silicone adhesive may be further modified by addition of organic esters, for example dodecyl acetate or octyl acetate, siloxylated diols, hydrocarbon plasticizers including but not limited to mineral oil, petrolatum, and waxes, and various agents for increasing cohesive strength including calcium or magnesium stearate, amorphous precipitated silica, fumed silica, and ethyl cellulose. In particular, addition of about 1% fumed silica with average particle size below about 100 microns to the polysiloxane pressure sensitive adhesive has been found to have a reinforcing effect and enhances the cohesiveness of the material.

Commercially available silicone adhesives that are suitable for the ostomy devices described above include the following.

TABLE 6

Silicone Pressure Sensitive Adhesives For Ostomy Pouch Couplings

| Manufacturer | Trade Name | One-Part Grades | Two Part Grades |
|---|---|---|---|
| Dow Corning | Bio-PSA ® | 7-410X, 7-420X, 7-430X, 7-440X, 7-450X, 7-460X, 7-4101, 7-4102, 7-4103, 7-4201, 7-4202, 7-4203, 7-4301, 7-4302, 7-4303, 7-4401, 7-4402, 7-4403, 7-4501, 7-4502, 4-4503, 7-4601, 7-4602, 7-4603 | 7-9800 |
| General Electric | Silgrip ® PSA | 518, 590, 595, 610, 6573A, 6574 | |
| Nusil Technology | NA | MED-1356 | |

Examples of Silicone Adhesive Formulations for Ostomy Couplings

Additional experiments were conducted to determine polysiloxane adhesive formulations suitable for ostomy device couplings. Approximately 15 grams of a silicone pressure sensitive adhesive was drawn over release coated film using a coating knife to control the thickness of the adhesive layer to between about 0.002 and about 0.004 inches. The adhesive was Bio-PSA® 7-4401 (available from Dow Corning Corporation) comprising a polysiloxane polymer treated with a silicate resin and dissolved in heptane. To remove the solvent from the adhesive layer the coating was placed in an oven and dried for 10 minutes at 70 C. The resultant adhesive layer was substantially solvent free and was then laminated with a closed cell foam comprised of a cross linked copolymer of ethylene and vinyl acetate (EVA). The adhesive coated foam prepared in this manner was similar to that described in WO99/26565 with the noted exception of the adhesive composition. Annular sections of the adhesive coated foam were cut from the sheet and welded to panels of plastic film and converted to ostomy pouches of the kind described in WO99/26565. Those skilled in the art will recognize that there are many suitable methods for preparing the coated foam and ostomy pouches described above and that the process in no way limits the invention disclosed herein. In a similar manner other silicone pressure sensitive adhesives were coated onto foam, converted into pouches, and tested for resistance to CSIF by the method described above. The results are shown in Table 7.

TABLE 7

Migration Results for Ostomy Couplings Comprised of Silicone Adhesive

| Example Number | Adhesive ID | Adhesive Component | CSIF Concentration Low | Medium | High |
|---|---|---|---|---|---|
| 1 | Bio-PSA ® 7-4401 | Polysiloxane | 0, 0, 0 | 0, 0, 0 | 0, 0, 0 |
| 2 | Bio-PSA ® 7-4501 | Polysiloxane | 0, 0, 0 | 0, 0, 0 | 0, 0, 0 |
| 3 | Bio-PSA ® 7-4601 | Polysiloxane | 0, 0, 0 | 0, 0, 0 | 0, 0, 0 |
| 4 | MED-1356 | Polysiloxane | 0, 0, 2 | 2, 1, 3 | 3, 3, 2, 1, 0 |

Data in Table 7 again shows the surprising improvement in resistance to intestinal fluid discovered for silicone adhesives compared with many other adhesives evaluated for ostomy coupling devices.

For the coupling device to be effective the peel strength of the pouch foam coupling from the wafer has limits beyond which the ostomy device as a whole will not be acceptable. The peel strength of the adhesive coated foam from the body attaching component should not be so low as to cause the attachment of the pouch to the wafer to be insecure or susceptible to leaks. A lower limit of acceptable peel strength for this purpose is believed to be about 0.5 Newtons/inch. Also, peel strength of the adhesive coated foam from the body attaching component should not be so high as to cause the wafer to be either loosened, or partially or completely removed from the skin by removal of the pouch from the wafer. Furthermore, the peel strength cannot be so high, or the anchorage of the adhesive layer to its substrate so low, as to cause adhesive to delaminate from the substrate (in this case an EVA foam), and remain on the body attaching component. If delamination occurs then the residue may prevent subsequent pouches from achieving a perfect seal to the adulterated attachment point, and that would defeat the reusability of the body attaching component. An upper limit of acceptable peel strength for this purpose is believed to be about 9.0 Newtons/inch, more preferably not more than about 6 Newtons/inch. To preserve the reusability of the pouch the peel strength should also be below the tensile strength of its substrate. The delamination force of the adhesive from the substrate of the coupling device preferably should be above about 6 Newtons/inch, and more preferably above about 9 Newtons/inch. Several methods exist to enhance anchorage of the adhesive to the substrate including increased temperature and pressure during lamination, and treatment with a corona discharge device.

The peel strength of silicone pressure sensitive adhesives can be controlled in several ways. One important factor that controls the peel strength of silicone adhesives is resin to polymer ratio. The preferred ratio of silicate resin to siloxane polymer should be between about 75/25 to about 25/75. The most preferred ratio of resin to polymer is 55/45. Another factor affecting peel strength is the thickness or coat weight of the adhesive. The examples of Table 7 are all at a thickness of between 0.002 and 0.004 inches thick, approximately equal to a coat weight of between about 50 and 100 grams per square meter (gsm). Below about 50 gsm the peel strength becomes dependent on coat weight. For example, for the EVA foam substrate described above, a coating of Bio-PSA 4601 of about 75 gsm has a peel strength of about 7.3 Newtons/inch from 9% EVA film, whereas at a coat weight of about 27 gsm the same adhesive has a peel strength of 5.6 Newtons/inch.

Another method for controlling peel strength is to further blend the crosslinked adhesive with additional silicate resin or a low molecular weight plasticizer, for example a silicone fluid (low molecular weight siloxane polymer). A mixing container was filled with Bio-PSA 7-4601 and blended by thoroughly stirring it with various low molecular weight polydimethylsiloxane (PDMS) oils according to the examples in Table 8. To remove the solvent from the adhesive layer the coating was placed in an oven and dried for 10 minutes at 70 C. The resultant adhesive layer was substantially solvent free and was then laminated with a closed cell foam comprised of a cross linked copolymer of ethylene and vinyl acetate (EVA). The adhesive coated foam prepared in this manner was similar to that described in WO99/26565 with the noted exception of the adhesive composition. The results in Table 8 show how adhesion was modified by blending PDMS oil of various viscosities (molecular weights) with the silicone pressure sensitive adhesive. Table 9 shows migration results for these examples. Except for example 8, all adhesives were coated to a thickness of between 0.002 and 0.004 inches.

TABLE 8

Silicone Adhesive Formulations with Modified Peel Strength

| Ex. No. | Adhesive ID | Adhesive Additive | Peel from Steel Per ASTM D3330 (Newtons/inch) | Peel from 9% VA content EVA Film (Newtons/inch) | Probe Tack per ASTM D2979 (grams, force) |
|---|---|---|---|---|---|
| 1 | Bio-PSA ® 7-4401 | None | 6.1 | 2.8 | 55 |
| 2 | Bio-PSA ® 7-4501 | None | 8.4 | 8.1 | 329 |
| 3 | Bio-PSA ® 7-4601 | None | 8.4 | 7.3 | 706 |
| 4 | MED-1356 (Nusil) | None | 8.8 | 6.9 | 234 |
| 5 | Bio-PSA ® 7-4401 | *9.4% PDMS Oil, 5000 cps | NA | 5.6 | 561 |
| 6 | Bio-PSA ® 7-4501 | *9.4% PDMS Oil, 5000 cps | NA | 4.7 | 678 |
| 7 | Bio-PSA ® 7-4601 | *9.4% PDMS Oil, 5000 cps | NA | 3.8 | 639 |
| 8 | Adhesive with Bio-PSA ® 7-4601 | None | NA | 5.4 | 492 |
| 9 | Bio-PSA ® 7-4601 | *5% PDMS Oil, 100 cps | NA | 4.9 | NA |
| 10 | Bio-PSA ® 7-4601 | *5% PDMS Oil, 20 cps | NA | 4.8 | NA |
| 11 | Bio-PSA ® 7-4601 | *5% PDMS Oil, 5000 cps | NA | 3.9 | NA |

*PDMS oil, 5000 cps is a low molecular weight polydimethylsiloxane polymer with viscosity of 5000 centipoise
NOTE 1: Other additives of PDMS oil have the viscosity indicted in centipoise.
NOTE 2: Peel testing performed as per ASTM D3330 using an ostomy wafer landing zone substrate comprised of poly(ethylene co-vinyl acetate) film with 9% vinyl acetate content.

TABLE 9

Migration Results for Silicone Adhesive Formulations

| Example Number | Adhesive ID | Adhesive Additive | CSIF Concentration Low | Medium | High |
|---|---|---|---|---|---|
| 1 | Bio-PSA ® 7-4401 | None | 0, 0, 0 | 0, 0, 0 | 0, 0, 0 |
| 2 | Bio-PSA ® 7-4501 | None | 0, 0, 0 | 0, 0, 0 | 0, 0, 0 |
| 3 | Bio-PSA ® 7-4601 | None | 0, 0, 0 | 0, 0, 0 | 0, 0, 0 |
| 4 | MED-1356 (Nusil) | None | 0, 0, 2 | 2, 1, 3 | 3, 3, 2, 1, 0 |
| 8 | Adhesive with Bio-PSA ® 7-4601 | None | 0, 0, 0 | 0, 0, 0 | 0, 0, 0 |
| 9 | Bio-PSA ® 7-4601 | *5% PDMS Oil, 100 cps | NA | NA | 0, 0, 0 |
| 10 | Bio-PSA ® 7-4601 | *5% PDMS Oil, 20 cps | NA | NA | 3, 4, 3 |
| 11 | Bio-PSA ® 7-4601 | *5% PDMS Oil, 5000 cps | NA | NA | 0, 0, 0 |

*PDMS oil, 5000 cps is a low molecular weight polydimethylsiloxane polymer with viscosity of 5000 centipoise
NOTE 1: Other additives of PDMS oil have the viscosity indicted in centipoise.

Pressure sensitive adhesive formulations comprising silicone polymers, optionally including additional silicate tackifiers and siloxane plasticizing oils with adhesion strength to a body attaching adherend between about 0.5 and about 9.0 Newtons/inch result in useful pouch attaching adhesives for coupling together ostomy device components. Those skilled in the art will recognize that the invention may include any of the siloxane polymers or silicate resins that can be made into pressure sensitive adhesives. The preferred adhesive for the devices of the invention is the polysiloxane pressure sensitive adhesive shown in the example 11 above.

The invention claimed is:

1. A two component adhesively coupleable ostomy device comprising a body attaching wafer component adhesively adhereable to the body and a pouch component, said two components being adhesively coupleable to and separable from each other along a pressure sensitive adhesive interface between said two components and positionable on the body to collect stomal fluid, said adhesive interface having a coat weight between about 10 grams per square meter and about 150 grams per square meter; wherein each of said components has a surface on opposite sides of said adhesive interface, one of said components having a closed cell foam surface, said adhesive interface being coated onto at least one of said surfaces, said two components releasably coupling to one another along said adhesive interface, said adhesive interface including one or more polysiloxanes, or one or more polysiloxanes and at least one silicate resin including their blends and reaction products, said adhesive interface being solvent-free, resealable and resistant to migration of stomal fluids into said adhesive interface.

2. The two component ostomy device of claim 1 wherein said adhesive interface includes between about 5% and about 65% hydrocolloids.

3. The two component ostomy device of claim 1 wherein said adhesive interface comprises one or more polysiloxanes selected from the group consisting of polydimethylsiloxane, polymethylphenylsiloxane, polydimethyldiphenylsiloxane, polydimethylmethylphenylsiloxane, polydiphenylmethylphenylsiloxane, polyalkylsiloxanes, polyorganosiloxanes, diorganopolysiloxane gums, or copolymers or combinations thereof.

4. The two component ostomy device of claim 1 wherein said adhesive interface is blended with a plasticizing oil.

5. The two component ostomy device of claim 4 wherein said plasticizing oil is polydimethylsiloxane.

6. The two component ostomy device of claim 1 wherein the polysiloxane or polysiloxanes are blended, treated or reacted with one or more silicate resins.

7. The two component ostomy device of claim 4 wherein any of the silicate resins comprises tetrakis (trimethylsiloxy) silicate, a trimethylsiloxy and hydroxy end-blocked silicate structure, or a silicate resin of the form tetrakis (trialkylsiloxy) silicate, optionally having silanol functionality or otherwise substituted with hydroxyl groups, and combinations thereof.

8. The two component ostomy device of claim 1 wherein said adhesive interface includes material having silanol functionality.

9. The two component ostomy device of claim 1 wherein the ratio of silicate resin to polysiloxane is between about 75:25 and about 25:75.

10. The two component ostomy device of claim 1 further including additional plasticizers, tackifiers, catalysts or other property modifiers including organic esters, siloxylated diols, hydrocarbon plasticizers, calcium or magnesium stearate, amorphous precipitated silica, fumed silica, and ethyl cellulose, or combinations thereof.

11. The two component ostomy device of claim 8 wherein the plasticizer, tackifier or other property modifier is a silanol, silane, siloxane, or silicate.

12. The two component ostomy device of claim 8 wherein the plasticizing component comprises from about 0.5 to about 20 percent of the solvent free dry adhesive formulation.

13. The two component ostomy device of claim 1 wherein said adhesive interface contains a medicament for treatment or protection of peristomal skin.

14. The two component ostomy device of claim 1 wherein one component includes an adhesive coated film or foam having a peel strength from a polyethylene or ethylene copolymer film between 0.5 and 9.0 Newtonslinch using the test method of ASTM 03330 wherein a stainless steel substrate is replaced by polyethylene or ethylene copolymer film.

15. The two component ostomy device of claim 1 wherein the peel strength of the adhered portions of the body attaching component and the pouch component is between 0.5 and 9.0 Newtons/inch as measured por ASTM 03330, wherein a stainless steel substrate is replaced by a film used on a component.

16. The two component ostomy device of claim 1 further comprising an adhesive for adhering said body attaching wafer component to the body, said adhesive including one or more polysiloxanes, or one or more polysiloxanes and at least one silicate resin including their blends and reaction products.

17. The two component ostomy device of claim 1 wherein said closed cell foam is a copolymer of ethylene and vinyl acetate.

* * * * *